(12) United States Patent
Williams et al.

(10) Patent No.: US 6,399,358 B1
(45) Date of Patent: Jun. 4, 2002

(54) HUMAN GENE ENCODING HUMAN CHONDROITIN 6-SULFOTRANSFERASE

(75) Inventors: Kevin Jon Williams, Wynnewood, PA (US); Ira Tabas, New City, NY (US)

(73) Assignee: Thomas Jefferson University, Philadelphia, PA (US)

(*) Notice: Subject to any disclaimer, the term of this patent is extended or adjusted under 35 U.S.C. 154(b) by 0 days.

(21) Appl. No.: 09/015,188

(22) Filed: Jan. 29, 1998

Related U.S. Application Data

(60) Provisional application No. 60/037,019, filed on Mar. 31, 1997, and provisional application No. 60/052,745, filed on Jul. 2, 1997.

(51) Int. Cl.$^7$ .......................... C12N 9/10; C12N 15/54
(52) U.S. Cl. .................. 435/252.3; 536/23.2; 435/193; 435/325; 435/300.1
(58) Field of Search .................. 536/23.2; 435/193, 435/320.1, 252.3, 325

(56) References Cited

U.S. PATENT DOCUMENTS

| | | | |
|---|---|---|---|
| 4,736,866 A | 4/1988 | Leder et al. ............... | 800/1 |
| 5,221,778 A | 6/1993 | Byrne et al. ............... | 800/2 |
| 5,223,610 A | 6/1993 | Burton et al. .............. | 536/24 |
| 5,910,581 A | * 6/1999 | Habuchi et al. ........... | 536/23.2 |
| 6,051,406 A | * 4/2000 | Fukuta et al. ............. | 435/101 |

FOREIGN PATENT DOCUMENTS

| | | |
|---|---|---|
| WO | WO 90/04632 | 5/1990 |
| WO | WO 93/07280 | 4/1993 |

OTHER PUBLICATIONS

M. Fukuta et al., "Molecular Cloning and Characterization of Human Keratan Sulfate Gal–6–Sulfotransferase", J. Biol. Chem. 272(51):32321–32328, Dec. 1997.*

H. Inoue et al. "Glycosaminoglycan sulfotransferases in human and animal sera", J.Biol. Chem. 261(10) 4460–9, Apr. 1986.*

GenBank Accession No. H16077, Jul. 1995.*

Adany et al., "Altered Expression of Chondroitin Sulfate Proteoglycan in the Stroma of Human Colon Carcinoma", J. Biol. Chem. 1990, 265:11389–11396.

Edwards, I.J. and Wagner, W.D., "Distinct Synthetic and Structural Characteristics of Proteoglycans Produced by Cultured Artery Smooth Muscle Cells of Atherosclerosis–susceptible Pigeons", J. Biol. Chem. 1988, 263:9612–9620.

Esko et al., "Sulfate Transport–deficient Mutants of Chinese Hamster Ovary Cells", J. Biol. Chem. 1986, 261, 15725–15733.

Fukata et al., "Molecular Cloning and Expression of Chick Chondrocyte Chondroitin 6–Sulfotransferase", J. Biol. Chem. 1995, 270:18575–18580.

Fuki et al., "The Syndecan Family of Proteoglycans", J. Clin. Invest. 1997, 100, 1611–1622.

Habuchi et al., "Changes in Proteoglycan Composition during Development of Rat Skin", J. Biol. Chem. 1986, 261:1031–1040.

Lennon et al., "The I.M.A.G.W. Consortium: An Integrated Molecular Analysis of Genomes and Their Expression", Genomics 1996, 33:151–152.

Mourao et al., "Spondyloepiphyseal Dysplasia, Chondroitin Sulfate Type: A Possible Defect of Paps—Chondroitin Sulfate Sulfotransferase in Humans", Biochem. Biophys. Res. Commun. 1981, 98:388–396.

Schonherr et al., "Effects of Platelet–derived Growth Factor and Transforming Growth Factor–$\beta$1 on the Synthesis of a Large Versican–like Chondroitin Sulfate Proteoglycan by Arterial Smooth Muscle Cells", J. Biol. Chem. 1991, 266:17640–17647.

Toledo et al., "Recessively Inherited, Late Onset Spondylar Dysplasia and Peripheral corneal Opacity With Anomalies in Urinary Mucopolysaccharides: A Possible Error of Chrondroitin–6–Sulfate Synthesis", Am. J. Med. Gen. 1978, 2:385–395.

Wasserman et al., "Use of thin–layer chromatography in the separation of disaccharides resulting from digestion of chondroitin sulphates with chondroitinases", J. Chromatogr. 1977, 136, 342–347.

Williams, K.J. and Tabas, I., "The Response–to–Retention Hypothesis of Early Athergenesis", Arterioscl. Thromb. Vasc. Biol. 1995, 15:551–561.

* cited by examiner

Primary Examiner—Rebecca E. Prouty
(74) Attorney, Agent, or Firm—ReedSmith LLP; William J. McNichol; Nanda P. B. A. Kumar

(57) ABSTRACT

Genes and polypeptides encoded thereby of human chondroitin 6-sulfotransferase are provided. Vectors and host cells comprising these genes and transgenic animals capable of expressing them are also provided. In addition, methods of identifying polymorphic chondroitin 6-sulfotransferase in humans and activators or inhibitors of this enzyme are provided.

11 Claims, 3 Drawing Sheets

```
ctgccgcactggctgg     gccagctgggnctggagacgctggt:  tgnggactcccc         60
agcttggagcagtccctccttgacctcactnctngagaagcagcccatgaaggtgcc         120
agccatgcaatgttcctggaaggccgtcctcctcttgcctggcctccactgccatcca         180
         M  Q  C  S  W  K  A  V  L  L  L  A  L  A  S  I  A  I  Q     19
gtacacggccatccgaccttcacngccaagtcctttcacacctgcccgggctggcaga         240
         Y  T  A  I  R  T  F  T  A  K  S  F  H  T  C  P  G  L  A  E  39
ggccgggctggccgagcgactgtgcgaggagagcccccaccttcgcctacaacctctcccg    300
         A  G  L  A  E  R  L  C  E  E  S  P  T  F  A  Y  N  L  S  R  59
caagacccacatcctcatcctggccaccacgcgcagcggctcctccttcgtgggccagct     360
         K  T  H  I  L  I  L  A  T  T  R  S  G  S  S  F  V  G  Q  L  79
cttcaaccagcacctggacgtcttctacctgtttgagcccctctaccacgtccagaacac     420
         F  N  Q  H  L  D  V  F  Y  L  F  E  P  L  Y  H  V  Q  N  T  99
gctcatccccgcttcacccagggcaagagcccggccgaccggcgggtcatgctaggcgc     480
         L  I  P  R  F  T  Q  G  K  S  P  A  D  R  R  V  M  L  G  A  119
cagccgcgacctcctgcggagcctctacgactgcgacctctacttcctggagaactacat     540
         S  R  D  L  L  R  S  L  Y  D  C  D  L  Y  F  L  E  N  Y  I  139
caagccgccgccggtcaaccacaccaccgacaggatcttccgccgcggggccagccgggt     600
         K  P  P  P  V  N  H  T  T  D  R  I  F  R  R  G  A  S  R  V  159
cctctgctccggcctgtgtgcgaccctccggggccagccgacctggtcctggaggaggg     660
         L  C  S  R  P  V  C  D  P  P  G  P  A  D  L  V  L  E  E  G  179
ggactgtgtgcgcaagtgcgggctactcaacctgaccgtggcggccgaggcgtgccgcga     720
         D  C  V  R  K  C  G  L  L  N  L  T  V  A  A  E  A  C  R  E  199
gcgcagccacgtggccatcaagacggtgcgcgtgcccgaggtgaacgacctgcgcgccct     780
         R  S  H  V  A  I  K  T  V  R  V  P  E  V  N  D  L  R  A  L  219
ggtggaagacccgcgattaaacctcaaggtcatccagctggtccgagaccccgcggcat     840
         V  E  D  P  R  L  N  L  K  V  I  Q  L  V  R  D  P  R  G  I  239
tctggcttcgcgcagcgagaccttccgcgacacgtaccggctctggcggctctggtacgg     900
         L  A  S  R  S  E  T  F  R  D  T  Y  R  L  W  R  L  W  Y  G  259
caccggggaggaaaccctacaacctggacgtgacgcagctgaccacggtgtgcgaggactt     960
         T  G  R  K  P  Y  N  L  D  V  T  Q  L  T  T  V  C  E  D  F  279
ctccaactccgtgtccaccggcctcatgcggccccgtggctcaagggcaagtacatgtt    1020
         S  N  S  V  S  T  G  L  M  R  P  P  W  L  K  G  K  Y  M  L  299
ggtgcgctacgaggacctggctcggaaccctatgaagaagaccgaggagatctacgggtt   1080
         V  R  Y  E  D  L  A  R  N  P  M  K  K  T  E  E  I  Y  G  F  319
cctgggcatcccgctggacagccacgtggcccgctggatccagaacaacacgcggggcga   1140
         L  G  I  P  L  D  S  H  V  A  R  W  I  Q  N  N  T  R  G  D  339
ccccaccctgggcaagcacaaatacggcacggtgcgaaactcggcggccacggccgagaa   1200
         P  T  L  G  K  H  K  Y  G  T  V  R  N  S  A  A  T  A  E  K  359
gtggcgcttccgcctctcctacgacatcgtggcctttgcccagaacgcctgccagcaggt   1260
         W  R  F  R  L  S  Y  D  I  V  A  F  A  Q  N  A  C  Q  Q  V  379
gctggcccagctgggctacaagatcgccgcctcggaggaggagctgaagaacccctcggt   1320
         L  A  Q  L  G  Y  K  I  A  A  S  E  E  E  L  K  N  P  S  V  399
cagcctggtggaggagcggggacttccgccccttctcgtgacccgggcggtgcgggtgggg   1380
         S  L  V  E  E  R  D  F  R  P  F  S  *                         411
gcgggaggcgcaaggtgtcggttttgataaaatggaccgttttaactgttgccttatta    1440
acccctccctctcccacctcatcttcgtgtccttcctgccccagctcaccccactccct    1500
tctgccccttttttgtctctgaaatttgcactacgtcttggacgggaatcactggggcag    1560
aggcgcctgaagtagggtcccgccccccaccccattcagacacatggatgttgggtc      1620
tctgtgcggacggtgacaatgtttacaagcancacatttacacatccacacacgcacacg   1680
ggcactcgcgaggcgacttctcaagcttttgaatgggtgagtggtcgggtatctagtttt   1740
tgcactgtcttactattcaaggtaagaggatacaaacaagaggaccacttgtctctaatt   1800
tatgaatggtgtccatcctttccccatccctgcctcctgccctgacgccatttccccc     1860
cttagagcagcgaaactgccccctcctgccgccttgcctgtcggtgaggcaggttttt    1920
actgtgaggtgaacgtggacctgtttctgtttccagtctgtggtgacgctgtctgtctgt   1980
ctgagtctcgtggccgccctggaccagtgatgactgatgaatcttatgagcttctgatt    2040
gatctcggggtccatctgtgatatttctttgtgccaaaagaaaaaaaagagtggatca     2100
gtttgctaaatgaacattgaaattgaaatgcttatntgtgttttctgtaaataaagag     2160
tgcaataaaaaaaaaaaaaaaaaaaaaaaa                                   2190
```

FIGURE 1

*NANTGTATACATCATATAGGCGAATTGGGCCTCTAGATGCATGCTCGAGCGGCCGCCAGTGTGAT*
*GGATATCTGCAGAATTCGGCTT*<u>GATGAGGATGTGGGTCTT</u>*GCGGGANAGGTTGTAGGCGAAGGTG*
GGGCTCTCCTCGCACAGTCGCTCGGCCAGCCCGGCCTCTGCCAGCCCGGGGCAGGTGTGAAAGGA
CTTGGCGGTGAAGGTGCGGATGGCCGTGTACTGGATGGCAATGGAGGCCAGGGCAAGGANGANGA
CGGCCTTCCAGGAACATTGCATGGCTGGGCACCTTCATGGGGCTGCTTCTCCAAGGGGTGAGGT‖
CTGTGGGCAAAGGCGGCCAGCGGTCAGGTGCCTCCACGGCGGGGGCACTGGCTTGTCCCTTGAA
NAGCCGGTCTCCAGGGGGCCCANGGAAAAGGCCCGGCTCCTGTCCAGTGCTCACCACACACCCTG
AAGACCTAAGCAGCTTCTACACTANACTACCGTTCTCTGGGGGACTCCTGGGAAGCTTTGGGGAN
CTGAACAAACATTCCTTGCACCCCAGGATTTAACCTGCGGACAGCTGCGGAAGCCTCTTATCCTG
AGCTCTGANTTCCTTAGAAGGGCCTCACGGGGCAAGAACCTGACTCCCCCTACTCCCACACTGAA
GGAAATGACGAAGGCCTGCCCCAAACACTGCCCCTCCTCACTTGCCAGCGTCTCCCACCCCCAC
NAACTGGCCCCCAATTTCTCCANGTTGTCCTCTTTTCCTCTGTCCTCTGCCCNTCCCCTAAGGGG
NAAAAAAAAAATCCCTATCAAAATGCCTCCCATCTGAACCCCAATCCCCCTNAACCACAAAGAA
NCCCTGCCNAAACCATNGTTCNGTTNAAACTGCCCACCACNGGCCAAGGCCAAGGTTGNAANAAC
TTTTTTCAANCCCCTTTCCAACTCCTTGGNATTCCAGGTTNACCCCTTTACNCCCAAATTTTAAA
CTNCTGGGGGCTTNTTTNAANTCCCCTAAAAAANTTCCCTGGGAACNNAAAAANAAAATTTCCCC
GGGTTCTCCNCAAAAAAAGCNANCCTTTCCCCAANCACCCCANGGGGTTTTTTTCCCCGNTTCCC
CCAAGGGNAAAAAGGGTTCCCNNCCCCTTGGNAAGNTTTAAAATAAANNCCCCCCTTAAAAACCC
AAAANTTAAAACTGGNCNCCCNAAAAAAANAATNTTTNGGGGAATTTTGGGGGGNCCCCCCCCC
CCTNAACCNCCCTTTTTTTCCCCCCCCNCCCCCCAAAAAN

FIGURE 2A

*NANCAAGCTATTTAGGTGACATATAGAATATCAAGCTATGCATCAAGCTTGGTACCGAGCTCGGA*
*TCCACTAGTAACGGCCGCCAGTGTGCTGGAATTCGGCTT*<u>TGGTGGCTGTGGACT</u>*CCCCAGCTTGG*
AGCAGTCCCTCTTTG‖GTAAGTGGTTGAACCCTCCTGTGTTCTCCCAGGAGCAGCCCCAGCCCC
CACTCAGGTCTGGTAGCTGAGCCAGCCTCCANAGAGGGTGCCTACAGGATGCTCAGGTGGGCTCC
TGGCCCCGGACTCTCAGCGGCCCCATTCGCTCTTTCTGCTTCTCCATGGTCCCTCCCCAGTCCCC
CTTCTGTGGGCAGAGGGGACACAGGAGGTAAGAGGGGAGGCCCCTGACTCCCTAAGATCTTCTTT
GCAGGCCAGTTCACTCTGTGTCAGTGGGGATTATGTCACCTCCATGGCCTGGACCCTTGTCCCTA
GAGACCAGGAACAGACCCTGGGTGCTGGAAGGGTTGCCTCTCAGCAGACCCTGGACATCTGTCT
CTGCTCCAGAGACTCTTAAAGACTCCACAAGCCCCAGAAGTCTACATCTGGANTAAGTGGTCACC
TGCATCCATNAATTGGAANGGGCTTGACACANTTGTCCACCTTGCCTGGCCGTGCTGGCANCTCA
CCGACCATGGTCTTGCANGGGTCTTCCTGCTCANGGGAATGGGGTCANATGAAGCATCTGATAN
GGAATCTTCTTTCCCTAAGGGATGGGCCNAAGGACNAAGAAAANAAGAACCCCTGGAAAAATGGG
CNCCAACCTCTTNGGGGTTGGAAAACCNTGGCCATTAAAGAANGGGCNTTTTTTGGGGCANGGCC
NCCTTCATTTCCCCAATNTTNGGAATTAGGGGGNANTCAGGGCTCTTNCCCCNTTNAAGCCCCC
CCTNANGGAACCCCCAAANCCCCNGGAAAAAAAAGGCNTCCCCNANCNTTTCCCCCNGGTTTNAA
ATCCCNNGGGGTTTCAAAGGAAANTTTTNTTTCCNCCCCCCAAACCCCCCAANAAAATTCCCCC
CAAAAAAANNGGTNATTCCAATTTTTTAAAACNNCCTTTANGGTTCTCCCNGGGNTTTTTTTTTT
AAACCCTNNAAAAANGNAAACCCGGGCCTTTTCCCCTNGGGCCCCCTTGNAAAAAACCGGCNCC
TTCCCCNGGGGNAAAAANCCCTTTTCCCCCCCCCTTGGAAAGGCCCCTNAAANNNCCCNNNN

FIGURE 2B

```
AGNAGCAGCGAAAACTGCCCCCTCCTGCCCGCCCTTGCCTGTCGGTGAGGCAGGTTTTTACTGTN
CAGGTGAACGTGGNACCTGTTTCTGTTTCCACTCTGTGGTGATGCTGTCTGTCTGTCTGAGTCTC
GTGGCCGCCCCTGGACCACTGATGACTGNTTATTNTTATGANCTTCTGATTGATCTCGGGGTCCA
NCTGTGATATTTCTTTGTGCCANAAAGAAAAAAAAANAGTGGATCAGTTTGCTAAATGAACATTG
AAATCGAAATGCTTNATCTGTGTTTTCNGTAAATAAAAGAGTGCAATAATCTCTGTGTGTGATTG
CANGACATNCNGAATGGGTACNAGAGGGCCTCAGCCGGGTCTGGGTGTNCCTANCTTTGGGGAGG
ACNNCGANACAGAGTGGAGGTGGGAATTAAATGACAAGTCTGCCTTTCAGAACTCTNGTCACCCT
CAACACTGAGTTCACTTCAGGTTTTTGTTTCGTCTTGTCTCGANACAGAATCTCCCTCTGTCNCC
CAGGCTGGAGTGCAATGGCCCCNTCTCNGCTCACTGCANCNCCNCCTCCCACGTTCAAGCCNTTC
TCCCNGCCTCACCTTCCCTAAATGACTGNGACTAACANGTNCCCTCTGGCCNCCCCGGCCCAACC
TTNTTTTCTCNCNCCGGTTTTCAACNNAAAANGGGNTTCCCCCCNTTTNTNCCCNCCCGCCCCCC
NAACCCCGAACCCTTGGGCCATCCCCNCTGNCTCACNCTNCCCAAATTNNNNGGGAANTNNCNNA
CTCTAACCCACCCCCCCCCCTCCTNTTCTTTTTTCCCCCTCCCCCNCTCTAAAANACNCGGTNAN
CTTANACCCCCNGGAAAAANTTTCAANTCNTCATCANCCNATTNTCTCGGCTNGGCCAAACCTAA
AATTACNTGGGAGGTTAAAANACNCCCCTCCNAACCCCTCCCTNCTCNCACTNNTCCCCCCTTC
ACTCTGGNNGNGTNNNGGGTTCCACAACCCNCACNGNAGNGGGAAACNCNCNCNGNGGNTNGGGT
TCCNCCCGGGNCNCTCGTCCCCCNCCCCACCANCCCCGCNAATTCTTCGCACTCTCTCNACNCCC
CGGCNCNNGTCTTCTCNCGCTCNTCCCCCNGGGNNAAAAACCCGCGGTNCTCCCCCCCCTNCCCN
NTNNTGGNATACTCTCCAGGGNTCGCCTCTNCCCTCTCCCNCNACTTCCTANCCCCANCAN
```

HUMAN GENE ENCODING HUMAN CHONDROITIN 6-SULFOTRANSFERASE

This application claims the benefit of U.S. Provisional Application No. 60/037,019, filed on Jan. 31, 1997 and U.S. Provisional Application No. 60/052,745, filed on Jul. 2, 1997.

INTRODUCTION

This invention was made in the course of research sponsored by the National Institutes of Health. The U.S. Government may have certain rights in this invention.

BACKGROUND OF THE INVENTION

Chondroitin sulfate is an important component of the extracellular matrix of animals. Chondroitin 6-sulfate (C6S), the form that is sulfated at position 6 of its N-acetylgalactosamine residues, has been implicated in several key roles in human biology, including development (Toledo et al. *Am. J. Med. Gen.* 1978, 2:385–395; Mourao et al, *Biochem. Biophys. Res. Commun.* 1981, 98:388–396; Habuchi et al. *J. Biol. Chem.* 1986, 261:1031–1040), cancer (Adany et al. *J. Biol. Chem.* 1990, 265:11389–11396), and atherosclerosis (Williams, K. J. and Tabas, I. *Arterioscl. Thromb. Vasc. Biol.* 1995, 15:551–561). The abundance of C6S is under genetic (Edwards, I. J. and Wagner, W. D. *J. Biol. Chem.* 1988, 263:9612–9620) and stimulatory (Schonherr et al. *J. Biol. Chem.* 1991, 266:17640–17647) control. Fukata et al. recently cloned the chick cDNA encoding C6ST, the essential enzyme in C6S synthesis (*J. Biol. Chem.* 1995, 270:18575–18580).

A human genomic DNA encoding C6ST has now been cloned and sequenced.

SUMMARY OF THE INVENTION

An object of the present invention is to provide a gene encoding human chondroitin 6-sulfotransferase.

Another object of the present invention is to provide vectors comprising genes encoding human chondroitin 6-sulfotransferase and host cells containing these vectors.

Yet another object of the present invention is to provide polypeptides encoded by human chondroitin 6-sulfotransferase.

Yet another object of the present invention is to provide nonhuman transgenic animals capable of encoding a gene of the present invention.

Yet another object of the present invention is to provide methods of identifying activators and inhibitors of expression, activities and biologic effects of human chondroitin 6-sulfotransferase.

Still another object of the present invention is to provide methods of identifying mutations in the genes encoding human chondroitin 6-sulfotransferase.

BRIEF DESCRIPTION OF THE FIGURES

FIG. 1 shows the human cDNA sequence (SEQ ID NO: 1) and deduced amino acid sequence (SEQ ID NO: 2) of human C6ST. In this Figure, the consensus sequence for signal peptide cleavage is indicated by a triangle. The four potential N-linked glycosylation sites are underlined. The tyrosine phosphorylation motifs are double underlined and the RGD sequence is overlined.

FIGS. 2A–2B show nucleic acid sequence of the intron in the 5' UTR of the human genomic C6ST clone, sequenced in each direction to show both splice sites and includes a vector sequence at the 5' end of each of the two sequences. FIG. 2A shows the antisense strand (SEQ ID NO: 3) while FIG. 2B shows the sense strand (SEQ ID NO: 4). Italics represent a portion of the nucleic acid sequence of the vector used. Underlined text represents sequences identical to the TP-RACE-8 (2A) and TP-RT-4 (2B) primers used to amplify the intron and flanking exonic sequences, using the C6ST genomic clone GS#12400 as a template. The intron-exon junctions are depicted by "∥": FIG. 2A contains the intronic 3' splice site, and FIG. 2B contains the intronic 5' splice site.

FIG. 3 shows the nucleic acid sequence of the 3' UTR followed immediately by the 3' downstream genomic sequence of the human genomic C6ST clone (SEQ ID NO: 5). The first base of the 3' genomic flanking sequence is designated by an arrowhead overtop "Ť".

DETAILED DESCRIPTION OF THE INVENTION

Human C6ST DNA has now been cloned. The nucleotide sequence of the cDNA (SEQ ID NO: 1) and its deduced amino acid sequence (SEQ ID NO: 2) are depicted in FIG. 1. This nucleotide sequence has been submitted to Genbank under Accession No. U65637. The nucleotide sequence shares 51% identity with the chick cDNA and 75% similarity with the chick amino acid sequence.

The full-length avian cDNA sequence was used to perform a computer search (Altschul et al. 1990) of the database of expressed sequence tags (dbEST) of the IMAGE consortium (Lennon et al. *Genomics* 1996, 33:151–152). Three high-homology human sequences were identified (IMAGE #40604-5 ', #48676-5', and #53039-5'), and the corresponding clones were obtained from Research Genetics, Inc. (Huntsville, Ala.). The inserts were fully sequenced and found to differ only in their 5' extent. Three additional dbEST sequences #K676-f, #43289-3', and #53039-3') were identified with this new sequence. The inserts of these clones were identical to the first three except for the 5' extent. The respective GenBank accession numbers for these dbEST sequences are R55609, H16077, and R16177 for the first set and R41023, H05595, and R15740 for the second set.

The longest insert (IMAGE #53039-5') was 1807 bp, but it lacked a start codon. Accordingly, the sequence was completed by 5' rapid amplification of cDNA ends using RNA templates from human chondrosarcoma, umbilical vein endothelial cells and saphenous vein smooth muscle cells. No sequence differences were observed amongst the three RNA sources. Sequences were assembled into a single contig which was analyzed for motifs and compared with the avian sequence.

The human cDNA of the present invention contains a single open reading frame of 1233 bp, corresponding to 411 amino acyl residues, with a predicted protein molecular weight of 46,714 Da. The unique in-frame start codon is a strong initiation site for translation and is homologous to the second of two potential start codons reported for the avian sequence (Fukata et al. *J. Biol. Chem.* 1995, 270 18575–18580). Nucleotide sequences, including 5' and 3' flanking regions, show 51% identity overall between the two species. This nucleotide sequence has been submitted to the Genbank database under accession number U65637.

A predicted amino acid sequence using the second potential avian start codon, shows 40% identity and 75% conservation. The human sequence contains an N-terminal signal peptide sequence thus explaining the presence of this enzyme extracellularly. The human sequence also has several potential sites for N-linked glycosylation. In addition, several phosphorylation motifs, including two tyrosine kinase phosphorylation sites, are present. The human sequence also contains an RGD motif which is believed to be significant when the molecule is outside the cell. See FIG. 1.

A probe containing the first 525 bp of the cDNA sequence of the human C6ST gene was prepared from a 5'-RACE clone obtained from a chondrosarcoma RNA template, referred to as clone #C81. Bases 1–383 were not identified in any of the IMAGE clones, while bases 384–525 overlapped with the 5' end of IMAGE clone #53039-5'. This probe was then used for automated screening of a human genomic P1 artificial chromosome (PAC) library by Genome Systems, Inc., St. Louis, Mo. In this library, the PAC vector is 16.5 kb, and the genomic inserts are typically approximately 120 kb. Two clones were identified with clone addresses of PAC-18-L22 and PAC-189-018, which correspond to GS control numbers of 12399 and 12400, respectively. Identification of these clones was verified by Southern Blot analysis of BamHI-generated fragments, hybridized with probes made from 5' and 3' segments of the cDNA. From these Southern blots, it was determined that the genomic clones have at least 2 kb of downstream DNA and at least 2 kb of DNA upstream of the cDNA probe.

A portion of the nucleic acid sequence of the genomic clone (gDNA) was then determined. Templates for automated sequences were prepared in two ways. First, pure plasmid preparations were made using protocols adapted to their large size in accordance with supplier's recommendations. Clone GS#12400 gave higher quality results than GS#12399. Second, after evidence was obtained indicating the position of an intron, one PCR primer upstream and another PCR primer downstream of the intron were synthesized based on the cDNA sequence. The sense primer, TP-RT-4, is a 15 bp sense sequence of cDNA, bp #42–56: TggTggCTgTggACT (SEQ ID NO: 6). The antisense primer, TP-RACE-8, is a 18 bp sequence antisense to cDNA bp #302–319: gATgAggATgTgggTCTT (SEQ ID NO: 7). The PCR reaction was carried out using genomic clone GS #12400 as the template. The PCR product was then inserted into the T/A cloning vector (Invitrogen, San Diego, Calif.) for sequencing. The insert size was approximately 1200–1300 bp, indicating an intron of approximately 950 bp. Primers for sequencing were synthesized commercially by Bioserve Biotechnologies, Laurel, Md, based on the C6ST cDNA sequence or on the T/A vector sequence. Additional sequenced portions of the genome include the intron of the 5' UTR, which has been sequenced in each direction to show both splice sites, depicted in FIG. 2A (antisense strand; SEQ ID NO:3) and FIG. 2B (sense strand; SEQ ID NO:4), and the 3' downstream genomic sequence (SEQ ID NO:5) depicted in FIG. 3.

Accordingly, the human C6ST gene structure from approximately base 42 of the cDNA to the poly-A signal consists of an initial exon limited to the 5' UTR, an intron of about 950 bp between cDNA bases 82 and 83, followed by an exon that encodes the rest of the 5' UTR plus the entire coding region and 3' UTR. In addition, it has been determined that there is no intron in the region of the gene corresponding to bases 1 to 42 of the cDNA sequence.

Based upon this structure, PCR primers have been designed which can be used with whole human chromosomal DNA to amplify regions of the gene. Representative primers are shown in the following Table.

TABLE

| Genomic Regions to amplify (#'s correspond to cDNA bases) | 5' Primer | 3' Primer |
| --- | --- | --- |
| #43–303 including intronic sequence | ggtggctgtggactcccca SEQ ID NO: 8 | ttgcgggagaggttgtag SEQ ID NO: 13 |
| 258–803 | gactgtgcgaggagagcc SEQ ID NO: 9 | ggtttaatcgcgggtctt SEQ ID NO: 14 |
| 759–1186 | aggtgaacgacctgcgcg SEQ ID NO: 10 | cgatcttgtagcccagct SEQ ID NO: 15 |
| 1234–1710 | ctttgcccagaacgcctg SEQ ID NO: 11 | cgaccactcacccattca SEQ ID NO: 16 |
| 1684–3' flanking region | actcgcgaggcgacttct SEQ ID NO: 12 | tgcaatcacacacagaga SEQ ID NO: 17 |

As will be obvious to those skilled in the art, additional primers can be routinely synthesized in accordance with the teachings herein. These primers are useful in a number of applications including, but not limited to, radiation hybrid panel mapping to determine chromosomal location and identify nearby microsatellite markers, and single-strand conformational polymorphism studies of human subjects and populations.

For example, two amplimers based on R15470, one of the six dbEST clones identified by high homology with chick C6ST, were analyzed on the Genebridge 4 panel by the Radiation Hybrid Transcript Mapping Consortium. These amplimers are stSG4330 and stSG3611. Both amplimers were mapped to chromosome 11. To identify their locations within chromosome 11, data vectors were submitted for three mapping runs on the Whitehead framework map, an lod 2.5 map (http://www-genome.wi.mit.edu). All three mapping runs localized the amplimers to the same region of chromosome 11, namely 4.5 or 6.51 centiRays (cR) from WI-4635. WI-4635 is a framework marker on the lod 2.5 map that has been placed 163.56 cR from the top of the chromosome 11 linkage group and is part of WC11.4, a singly linked YAC contig. Examination of chromosome 11 contigs anchored on the integrated map revealed several nearby markers with simple sequence repeats known or likely to be polymorphic. These markers, or any other very nearby markers, can be used in linkage studies of the C6ST gene.

Further, based upon these data, elucidation of the complete gene structure including, but not limited to, the regions corresponding to bases 1–41 of the cDNA and upstream and additional downstream genomic sequences can be performed. For example, it has been determined that there are no introns in the region of the gene corresponding to bases 1 to 42 of the cDNA sequence.

Using a genomic clone as a template, the entire C6ST coding region was amplified via PCR in one piece and then ligated into a pcDNA3 expression vector (Invitrogen, San Diego, Calif.). This vector contains a CMV promoter which drives eukaryotic expression and a neomycin resistance gene. This construct was introduced into Chinese Hamster Ovarian (CHO) cells by calcium phosphate transfection and stable transfectants were selected with G418. Artifacts from clonal variation were minimized by propagating two mixed lines and three clonal lines. Wild-type CHO cells and one clonal CHO line that has been transfected with an irrelevant cDNA, pFcR-Synd1 described by Fuki et al. *J. Clin. Invest.* 1997, 100, 1611–1622 served as controls. Expression of the constructs was verified by Northern blot, which showed abundant message in all transfected cells except controls. Homogenates of the cells were then prepared, and the C6ST and chondroitin 4-sulfotransferase (C4ST) enzymatic activities were assessed by incubation in the presence of [$^{35}$S] PAPS (a sulfate donor) and nsulfated chondroitin (a sulfate acceptor), followed by the complete enzymatic digestion of the newly sulfated chondroitin into disaccharides in accordance with procedures described by Fukuta et al. *J. Biol. Chem.* 1995, 270, 18575–18580. The labeled disaccharides, [$^{35}$S] ΔDi-6S and [$^{35}$S] ΔDi-4S, which indicate the enzymatic activities of C6ST and C4ST, respectively, were then separated by thin-layer chromatography using plates coated with microcrystalline cellulose (Analtech, Newark, Del.) as described by Wasserman et al. *J. Chromatogr.* 1977, 136, 342–347, and autoradiography was performed using a PhosphorImager (Molecular Dynamics, Sunnyvale, Calif.).

It was found that wild-type CHO have abundant endogenous C4ST activity but very little C6ST activity which is consistent with reports by Esko et al. *J. Biol. Chem.* 1986, 261, 15725–15733 that the GAGS made by these cells have a low C6S:C4S ratio. The clonal control was exactly the same. In contrast, cell homogenates of all mixed and clonal lines transfected with the C6ST expression vector showed C6ST activity that was equal to or greater than the C4ST activity. The C6ST to C4ST ratio in the transfected lines over control cells was up to 14 fold. Thus, this cDNA encodes human C6ST. Separate studies using keratan sulfate as the sulfate acceptor showed that, similar to the chick enzyme, the human molecule also possesses keratan sulfate sulfotransferase (KSST) activity. As an additional control, incubations of cell homogenates with [$^{35}$S] PAPS but no sulfate acceptor showed essentially no product. It is believed that the human. enzyme is also capable of sulfating sialyl lactosamine oligosaccharides thus making it a candidate for the biosynthesis of sulfated Lewis X ligand for L-selectin.

Genes of the present invention and the polypeptides encoded thereby are useful in the molecular study of human extracellular matrix. For the purpose of the present invention, by "gene" it is meant genomic sequences which have been isolated and identified and may also include related nucleic acids sequences thereof. By "nucleic acid sequence" it is meant to include, but is not limited to, the cDNA and gDNA encoding C6ST and fragments thereof, along with nucleic acid sequences or fragments thereof with a different sequence, which as a result of the redundancy of the genetic code, also encode C6ST. Also included are regulatory sequences from the gDNA or cDNA such as, but not limited to, upstream and downstream sequences, intronic sequences and sequences from the 5' and 3' UTRs. Genes of the present invention may be in the form of DNA, including cDNA and gDNA obtained by cloning or produced by chemical synthetic techniques or a combination thereof, or in the form of RNA, such as mRNA. The DNA may be double stranded or single stranded. Single stranded DNA may be the coding or sense strand or the noncoding or antisense strand. The present invention also relates to variants of these genes which may be naturally occurring, i.e., allelic variants, or mutants prepared by well known mutagenesis techniques. The term "polypeptide" is used herein to refer to any peptide or protein comprising two or more amino acids joined to each other in a linear chain by peptide bonds which is encoded by a gene of the present invention. As used herein, the term refers to both short chains, which also commonly are referred to in the art as peptides, oligopeptides and oligomers, for example, and to longer chains, which generally are referred to in the art as proteins, of which there are many types. Such polypeptides can be prepared recombinantly in a host cell using a vector comprising a gene of the present invention. Alternatively, one the amino acid sequence of an encoded polypeptide is determined, the polypeptide can be prepared synthetically. By the term "polypeptide" it is also meant to encompasses modified polypeptides, wherein the modification occurs either by natural processes, such as processing and other post-translational modifications, or by chemical modification techniques which are well known to the art. Such modifications are well known to those of skill and have been described in great detail in the scientific literature.

In on embodiment, the genes of the present invention are useful in studying the biologic functions of C6S. C6S is known to bind low-density lipoprotein (LDL) more avidly than chondroitin 4-sulfate (C4S) does. It is believed that this binding could play a role in the retention and accumulation of cholesterol-rich lipoproteins in the arterial wall, thus leading to the development of arteriosclerosis. Accordingly, C6ST expression in the arterial wall may be a factor in the development of atherosclerosis. The genes of the present invention will be useful in ascertaining and evaluating the role C6ST plays in atherosclerosis. For example, using these genes it can now be determined if C6ST is polymorphic in humans. If so, it can then be determined if one polymorph or another is associated with premature coronary artery disease, or delayed disease. The genes of the present invention could then be used in screening tests for detecting these polymorphs. In addition, the genes can be used in identifying potential therapeutics, i.e., inhibitors of the enzyme or modulators of gene expression. Techniques using nucleic acid sequences to identify potential therapeutics include, but are not limited to; identification of regulatory motifs in the genomic sequence that can be exploited in therapeutic intervention; identification of structures in the C6ST protein based on the amino acyl sequences deduced from the cDNA and gDNA; and expression of C6ST protein or protein fragments, using cDNA or gDNA sequences or fragments thereof in prokaryotes or eukaryotes, for production of material for determination of additional biological effects, raising antibodies and screening large numbers of potential pharmacological inhibitors or activators of the C6ST molecule.

The C6ST enzyme has other functions as well. For example, there is a kindred in Brazil that appears to have an abnormality in the enzyme that leads to skeletal malformation. C6S is a major component of cartilage and other tissues. This enzyme also catalyzes the sulfation of keratan sulfate. In addition, C6S has also been implicated in development, cancer and other cellular interactions. Knowledge of the sequence of the gene encoding C6ST will thus be useful in identifying potential therapeutics for modulating these other biological functions of C6S.

Host cells can be genetically engineered to contain genes of the present invention so that the cells express the C6ST enzyme and/or contain potential regulatory sequences from the genomic DNA, including but not limited to, upstream and downstream sequences, intronic sequences and sequences from the 5' and 3' UTRs. Nucleic acid sequences of the gene may be introduced into host cells using any well known technique including, but not limited to, infection, transduction, transfection, transvection and transformation. Such techniques are reviewed, for example, in Sambrook et al., *Molecular Cloning, A Laboratory Manual*, 2nd Ed., Cold Spring Harbor Laboratory Press, Cold Spring Harbor, 1989, N.Y. The nucleic acid sequences can be introduced alone or with other nucleic acid sequences such as those encoding a selectable marker and/or reporter sequence. For example, a nucleic acid sequence of the gene of the present invention can be joined to a vector containing a selectable marker for propagation in a host. The vector construct is then introduced into the host cell. Selection of appropriate vectors and promoters for expression in a host cell is a well known procedure and the requisite techniques for construction of expression vectors, introduction of the vector into the host and expression in the host are routine skills in the art. Host cells which can be used include higher eukaryotic cell, such as a mammalian cell, a lower eukaryotic cell, such as a yeast cell, or a prokaryotic cell, such as a bacterial cell. Thus, the present invention also includes vectors comprising genes of the present invention and host cells containing these vectors.

Host cells and polypeptides of the present invention may be employed in a screening process for compounds which activate (activators or agonists) or inhibit (inhibitors or antagonists) activation, expression and/or biologic effects of the enzyme. Compounds which activate or inhibit expression and/or activities of the enzyme may be identified by monitoring enzyme levels or activity in the host cells or surrounding matrix of the host cells before and after contact with the compound. Compounds which act as agonists will increase levels or activity of the enzyme or biologic effects of the enzyme while antagonists will decrease levels, activity or biologic effects of the enzyme. For example, contacting cells with an antisense oligonucleotide targeted to a portion of a gene of the present invention may inhibit expression of the C6ST enzyme in the cells. Compounds which activate or inhibit the enzyme directly can also be identified in these cells by monitoring activity of the enzyme in the cell in the presence or absence of a test compound. There are several endpoints relating to enzyme levels, activity or biologic effect that can be measured in a host cell expressing C6ST or the surrounding matrix to identify agonists or antagonists. For example, cellular content of C6ST mRNA and rates of mRNA synthesis, i.e., gene transcription, and rates of mRNA breakdown, i.e., message stability, can be measured. Alternatively, the rate of synthesis of C6ST protein, i.e., translation rates and translation efficiency, can be measured using an antibody raised against short peptides or longer segments synthesized based upon the cDNA sequence. Enzymatic activity can also be determined by measuring the transfer of sulfate from phosphoadenosine phosphosulfate onto chondroitin and/or keratan. Alternatively, keratan sulfate transferase (KSST) activity or sulfation of sialyl lactosamine oligosaccharides can be measured. Polypeptides of the present invention can also be used in screening processes to monitor enzyme activities in the presence and absence of a compound suspected of being an activator or inhibitor of the C6ST enzyme. In addition, biological effects of such sulfation, such as binding affinity of cellular chondroitin to LDL, can be determined in both polypeptides and host cells. For example, with more C6ST expression, a higher ratio of C6S to C4S is expected thus resulting in better binding of the chondroitin sulfate to LDL. In addition, contents of C6S and C4S, as well as keratan sulfate, can be measured.

Vectors comprising genes of the present invention are also useful in the development of transgenic animals capable of expressing human C6ST or fragments or variants thereof, as well as knockout animals made by homologous recombination to disrupt the endogenous C6ST gene. Transgenic animals are used routinely in the assessment of new therapeutic compositions and in carcinogenicity testing as exemplified by U.S. Pat. No. 5,223,610. These animals are also used in the development of predictive animal models for human disease states as exemplified in U.S. Pat. No. 5,221, 778. Transgenic animals have now been developed for assessing Alzheimer's disease (WO 9307280), multi-drug resistance to anticancer agents (WO 9004632), and carcinogenic substances (U.S. Pat. No. 4,736,866). Accordingly, methods of generating transgenic animals are well known to those skilled in the art.

While the present invention has been described in terms of specific embodiments, it is understood that variations and modifications will occur to those skilled in the art. Accordingly, only such limitations as appear in the appended claims should be placed upon the instant invention.

What is claimed is:

1. A recombinant polynucleotide segment, comprising a polynucleotide sequence, wherein the polynucleotide sequence (a) is SEQ ID NO:1, or (b) is the full complement of the entire length of SEQ ID NO:1.

2. A vector comprising the recombinant polynucleotide segment of claim 1.

3. A host cell transformed with the vector claim 2.

4. A recombinant polynucleotide segment comprising a polynucleotide sequence, wherein the polynucleotide sequence is (a) nucleotides 125 to 1360 of SEQ ID NO:1;

b) nucleotides 179 to 1360 of SEQ ID NO:1; or (c) the full complement of the entire length of (a) or (b).

5. A vector comprising the recombinant polynucleotide segment of claim 4.

6. A host cell transformed with the vector of claim 5.

7. A recombinant polynucleotide segment, comprising a polynucleotide sequence, wherein the polynucleotide sequence (a) encodes a polypeptide comprising the amino acid sequence of SEQ ID NO:2, or (b) is the full complement of the entire length of a reference sequence that encodes a polypeptide comprising the amino acid sequence of SEQ ID NO:2.

8. A vector comprising the recombinant polynucleotide segment of claim 7.

9. The vector of claim 8, wherein the recombinant polynuclotide segment encodes the polypeptide.

10. A host cell transformed with the vector of claim 8.

11. A host cell transformed with the polynucleotide segment of claim 7.

* * * * *

UNITED STATES PATENT AND TRADEMARK OFFICE
CERTIFICATE OF CORRECTION

PATENT NO.    : 6,399,358 B1                                               Page 1 of 1
DATED         : June 4, 2002
INVENTOR(S)   : Kevin Jon Williams and Ira Tabas It is certified that error appears in the above-identified patent and that said Letters Patent is hereby corrected as shown below:

Drawings,
Figure 1, line 1 should read as follows:
-- ctgccgcactggctgggactgccagctgggcctggagacgctggtggctgtggactcccc      60 --

Signed and Sealed this

Twenty-fourth Day of September, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO.      : 6,399,358 B1
DATED           : June 4, 2002
INVENTOR(S)     : Kevin Jon Williams and Ira Tabas It is certified that error appears in the above-identified patent and that said Letters Patent is hereby corrected as shown below:

Drawings,
Figure 1, line 1 should read as follows:
-- ctgccgcactggctgggactgccagctgggcctggagacgctggtggctgtggactcccc     60 --

Signed and Sealed this

Fifteenth Day of October, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,399,358 B1
DATED : June 4, 2002
INVENTOR(S) : Williams et al.

It is certified that error appears in the above-identified patent and that said Letters Patent is hereby corrected as shown below:

<u>Title page,</u>
Item [73], Assignee, after "Thomas Jefferson University, Philadelphia, PA (US)" insert -- Columbia University, New York, NY (US) --

Signed and Sealed this

Sixteenth Day of March, 2004

JON W. DUDAS
*Acting Director of the United States Patent and Trademark Office*

SEQUENCE LISTING

```
<160> NUMBER OF SEQ ID NOS: 17

<210> SEQ ID NO 1
<211> LENGTH: 2190
<212> TYPE: DNA
<213> ORGANISM: Homo sapiens

<400> SEQUENCE: 1
ctgccgcact ggctgggact gccagctggg cctggagacg ctggtggctg tggactcccc      60
agcttggagc agtccctctt tgacctcacc ccttggagaa gcagccccat gaaggtgccc     120
```

-continued

```
agccatgcaa tgttcctgga aggccgtcct cctccttgcc ctggcctcca ttgccatcca      180
gtacacggcc atccgcacct tcaccgccaa gtcctttcac acctgccccg ggctggcaga      240
ggccgggctg gccgagcgac tgtgcgagga gagccccacc ttcgcctaca acctctcccg      300
caagacccac atcctcatcc tggccaccac gcgcagcggc tcctccttcg tgggccagct      360
cttcaaccag cacctggacg tcttctacct gtttgagccc ctctaccacg tccagaacac      420
gctcatcccc gcttcaccc agggcaagag cccggccgac cggcgggtca tgctaggcgc      480
cagccgcgac ctcctgcgga gcctctacga ctgcgacctc tacttcctgg agaactacat      540
caagccgccg ccggtcaacc acaccaccga caggatcttc cgccgcgggg ccagccgggt      600
cctctgctcc cggcctgtgt gcgaccctcc ggggccagcc gacctggtcc tggaggaggg      660
ggactgtgtg cgcaagtgcg ggctactcaa cctgaccgtg gcggccgagg cgtgccgcga      720
gcgcagccac gtggccatca agacggtgcg cgtgcccgag gtgaacgacc tgcgcgccct      780
ggtggaagac ccgcgattaa acctcaaggt catccagctg gtccgagacc cccgcggcat      840
tctggcttcg cgcagcgaga ccttccgcga cacgtaccgg ctctggcggc tctggtacgg      900
caccgggagg aaaccctaca acctggacgt gacgcagctg accacggtgt gcgaggactt      960
ctccaactcc gtgtccaccg gcctcatgcg gccccgtgg ctcaagggca agtacatgtt     1020
ggtgcgctac gaggacctgg ctcggaaccc tatgaagaag accgaggaga tctacgggtt     1080
cctgggcatc ccgctggaca gccacgtggc ccgctggatc cagaacaaca cgcggggcga     1140
ccccacccct ggcaagcaca aatacggcac cgtgcgaaac tcggcggcca cggccgagaa     1200
gtggcgcttc cgcctctcct acgacatcgt ggcctttgcc cagaacgcct gccagcaggt     1260
gctggcccag ctgggctaca agatcgccgc ctcggaggag gagctgaaga cccctcggt     1320 cagcctggtg gaggagcggg acttccgccc cttctcgtga cccgggcggt gcgggtgggg     1380
gcgggaggcg caaggtgtcg gttttgataa aatggaccgt ttttaactgt tgccttatta     1440
acccctccct ctcccacctc atcttcgtgt ccttcctgcc cccagctcac cccactccct     1500 tctgccctt ttttgtctct gaaatttgca ctacgtcttg gacgggaatc actggggcag     1560
agggcgcctg aagtagggtc ccgccccccc cacccccattc agacacatgg atgttgggtc     1620
tctgtgcgga cggtgacaat gtttacaagc accacattta cacatccaca cacgcacacg     1680
ggcactcgcg aggcgacttc tcaagctttt gaatgggtga gtggtcgggt atctagtttt     1740
tgcactgtct tactattcaa ggtaagagga tacaaacaag aggaccactt gtctctaatt     1800
tatgaatggt gtccatcctt tccccatccc tgcctcctgc ccctgacgcc catttccccc     1860
cttagagcag cgaaactgcc ccctcctgcc cgccttgcc tgtcggtgag gcaggttttt     1920
actgtgaggt gaacgtggac ctgtttctgt ttccagtctg tggtgatgct gtctgtctgt     1980
ctgagtctcg tggccgcccc tggaccagtg atgactgatg aatcttatga gcttctgatt     2040
gatctcgggg tccatctgtg atatttcttt gtgccaaaaa gaaaaaaaa gagtggatca     2100 gtttgctaaa tgaacattga aattgaaatg ctttatctgt gttttctgta aataaaagag     2160
tgcaataaaa aaaaaaaaaa aaaaaaaaa                                        2190
```

<210> SEQ ID NO 2
<211> LENGTH: 411
<212> TYPE: PRT
<213> ORGANISM: Homo sapiens

<400> SEQUENCE: 2

Met Gln Cys Ser Trp Lys Ala Val Leu Leu Leu Ala Leu Ala Ser Ile

-continued

```
  1               5                    10                   15
Ala Ile Gln Tyr Thr Ala Ile Arg Thr Phe Thr Ala Lys Ser Phe His
                20                  25                  30

Thr Cys Pro Gly Leu Ala Glu Ala Gly Leu Ala Glu Arg Leu Cys Glu
            35                  40                  45

Glu Ser Pro Thr Phe Ala Tyr Asn Leu Ser Arg Lys Thr His Ile Leu
        50                  55                  60

Ile Leu Ala Thr Thr Arg Ser Gly Ser Ser Phe Val Gly Gln Leu Phe
65                  70                  75                  80

Asn Gln His Leu Asp Val Phe Tyr Leu Phe Glu Pro Leu Tyr His Val
                85                  90                  95

Gln Asn Thr Leu Ile Pro Arg Phe Thr Gln Gly Lys Ser Pro Ala Asp
                100                 105                 110

Arg Arg Val Met Leu Gly Ala Ser Arg Asp Leu Leu Arg Ser Leu Tyr
            115                 120                 125

Asp Cys Asp Leu Tyr Phe Leu Glu Asn Tyr Ile Lys Pro Pro Val
        130                 135                 140

Asn His Thr Thr Asp Arg Ile Phe Arg Arg Gly Ala Ser Arg Val Leu
145                 150                 155                 160

Cys Ser Arg Pro Val Cys Asp Pro Pro Gly Pro Ala Asp Leu Val Leu
                165                 170                 175

Glu Glu Gly Asp Cys Val Arg Lys Cys Gly Leu Leu Asn Leu Thr Val
                180                 185                 190

Ala Ala Glu Ala Cys Arg Glu Arg Ser His Val Ala Ile Lys Thr Val
            195                 200                 205

Arg Val Pro Glu Val Asn Asp Leu Arg Ala Leu Val Glu Asp Pro Arg
210                 215                 220

Leu Asn Leu Lys Val Ile Gln Leu Val Arg Asp Pro Arg Gly Ile Leu
225                 230                 235                 240

Ala Ser Arg Ser Glu Thr Phe Arg Asp Thr Tyr Arg Leu Trp Arg Leu
                245                 250                 255

Trp Tyr Gly Thr Gly Arg Lys Pro Tyr Asn Leu Asp Val Thr Gln Leu
            260                 265                 270

Thr Thr Val Cys Glu Asp Phe Ser Asn Ser Val Ser Thr Gly Leu Met
            275                 280                 285

Arg Pro Pro Trp Leu Lys Gly Lys Tyr Met Leu Val Arg Tyr Glu Asp
290                 295                 300

Leu Ala Arg Asn Pro Met Lys Lys Thr Glu Glu Ile Tyr Gly Phe Leu
305                 310                 315                 320

Gly Ile Pro Leu Asp Ser His Val Ala Arg Trp Ile Gln Asn Asn Thr
                325                 330                 335

Arg Gly Asp Pro Thr Leu Gly Lys His Lys Tyr Gly Thr Val Arg Asn
            340                 345                 350

Ser Ala Ala Thr Ala Glu Lys Trp Arg Phe Arg Leu Ser Tyr Asp Ile
            355                 360                 365

Val Ala Phe Ala Gln Asn Ala Cys Gln Gln Val Leu Ala Gln Leu Gly
        370                 375                 380

Tyr Lys Ile Ala Ala Ser Glu Glu Leu Lys Asn Pro Ser Val Ser
385                 390                 395                 400

Leu Val Glu Glu Arg Asp Phe Arg Pro Phe Ser
                405                 410
```

<210> SEQ ID NO 3

-continued

<211> LENGTH: 1274
<212> TYPE: DNA
<213> ORGANISM: Homo sapiens
<220> FEATURE:
<220> FEATURE:
<223> OTHER INFORMATION: "n" at locations 112, 255 and 258 is "g";
      "n" at the remaining locations is "unknown"

<400> SEQUENCE: 3

| | | |
|---|---|---|
| nantgtatac atcatatagg cgaattgggc ctctagatgc atgctcgagc ggccgccagt | 60 |
| gtgatggata tctgcagaat tcggcttgat gaggatgtgg gtcttgcggg anaggttgta | 120 |
| ggcgaaggtg gggctctcct cgcacagtcg ctcggccagc ccggcctctg ccagcccggg | 180 |
| gcaggtgtga aaggacttgg cggtgaaggt gcggatggcc gtgtactgga tggcaatgga | 240 |
| ggccagggca agganganga cggccttcca ggaacattgc atggctgggc accttcatgg | 300 |
| ggctgcttct ccaaggggtg aggtctgtgg gcaaaggcgg ccagcggtca ggtgcctcca | 360 |
| cggcggggc actggcttgt cccttggaan agccggtctc caggggccc anggaaaagg | 420 |
| cccggctcct gtccagtgct caccacacac cctgaagacc taagcagctt ctacactana | 480 |
| ctaccgttct ctgggggact cctgggaagc tttgggganc tgaacaaaca ttccttgcac | 540 |
| cccaggattt aacctgcgga cagctgcgga agcctcttat cctgagctct ganttcctta | 600 |
| gaagggcctc acgggcaag aacctgactc ccccactcc cacactgaag gaaatgacga | 660 |
| aggcctgccc caaacactgc ccctcctcac ttgccagcgt ctcccacccc ccacnaactg | 720 |
| gcccccaatt tctccangtt gtcctctttt cctctgtcct ctgcccntcc cctaaggggn | 780 |
| aaaaaaaaaa tccctatcaa aatgcctccc atctgaaccc caatcccct naaccacaaa | 840 |
| agaancctg ccnaaaccat ngttcngttn aaactgccca ccacnggcca aggccaaggt | 900 |
| tgnaanaact tttttcaanc cccttccaa ctccttggna ttccaggttn acccctttac | 960 |
| ncccaaattt taaactnctg ggggcttntt tnaantcccc taaaaaantt ccctgggaac | 1020 |
| nnaaaaanaa aatttccccg ggttctccnc aaaaaaagcn ancctttccc caancacccc | 1080 |
| angggtttt tttccccgnt tcccccaagg gnaaaagg ttccnncc cttggnaagn | 1140 |
| tttaaaataa annccccct taaaaaccca aaanttaaaa ctggncnccc cnaaaaaaan | 1200 |
| aatntttngg ggaattttgg ggggncccc ccccctnaa ccncccttt ttccccccc | 1260 |
| cncccccaa aaan | 1274 |

<210> SEQ ID NO 4
<211> LENGTH: 1233
<212> TYPE: DNA
<213> ORGANISM: Homo sapiens
<220> FEATURE:
<223> OTHER INFORMATION: "n" at all locations is "unknown"

<400> SEQUENCE: 4

| | | |
|---|---|---|
| nancaagcta tttaggtgac atatagaata tcaagctatg catcaagctt ggtaccgagc | 60 |
| tcggatccac tagtaacggc cgccagtgtg ctggaattcg gctttggtgg ctgtggactc | 120 |
| cccagcttgg agcagtccct ctttggtaag tggttgaacc ctcctgtgtt ctccccagga | 180 |
| gcagccccag cccccactca gctctggtag ctgagccagc ctccanagag ggtgcctaca | 240 |
| ggatgctcag gtgggctcct ggccccggac tctcagcggc ccattcgct ctttctgctt | 300 |
| ctccatggtc cctccccagt ccccttctg tgggcagagg ggacacagga ggtaagaggg | 360 |
| gaggcccctg actccctaag atcttctttg caggccagtt cactctgtgt cagtggggat | 420 |
| tatgtcacct ccatggcctg gacccttgtc cctagagacc aggaacagac cctgggtgct | 480 |

-continued

```
gggaagggtt gcctctcagc agaccctgga catctgtctc tgctccagag actcttaaag    540
actccacaag ccccagaagt ctacatctgg antaagtggt cacctgcatc catnaattgg    600 aanggcttg  acacanttgt ccaccttgcc tggccgtgct ggcanctcac cgaccatggt    660
cttgcanggg tcttcctgct canggggaatg gggtcanatg gaagcatctg atanggaatc   720
ttctttccct aagggatggg ccnaaggacn aagaaaanaa gaaccccctgg aaaaatgggc   780 nccaacctct tngggggttgg aaaaccntgg ccattaaaga angggcntt  tttggggcan   840 ggccnccttc atttccccaa tnttnggaat taggggggnan tcagggctct tnnccccntt   900 naagccccc  ctnanggaac ccccaaaance ccnggaaaaa aaaggcntcc ccnancnttt   960
cccccnggtt tnaaatcccn ngggggtttca aaggaaantt ttntttccnc cccccccaaac  1020 cccccaanaa aattcccccc aaaaaaanng gtnattccaa ttttttaaaa cnnccttan    1080 ggttctcccn gggnttttt  ttttaaaaccc tnnaaaaang naaacccggg cctttttcccc  1140 tngggggcccc cttgnaaaaa accggcncct tccccnggggg naaaaancc  ttttccccc   1200 ccccttggaa aggccccctna aannnncccn nnn                                1233
```

<210> SEQ ID NO 5
<211> LENGTH: 1231
<212> TYPE: DNA
<213> ORGANISM: Homo sapiens
<220> FEATURE:
<223> OTHER INFORMATION: "n" at all  locations is "unknown"

<400> SEQUENCE: 5

```
agnagcagcg aaaactgccc cctcctgccc gcccttgcct gtcggtgagg caggttttta    60
ctgtncaggt gaacgtggna cctgtttctg tttccactct gtggtgatgc tgtctgtctg   120
tctgagtctc gtggccgccc ctggaccact gatgactgnt tattnttatg ancttctgat   180
tgatctcggg gtccanctgt gatatttctt tgtgccanaa agaaaaaaaa anagtggatc   240
agtttgctaa atgaacattg aaatcgaaat gcttnatctg tgttttcngt aaataaaaga   300
gtgcaataat ctctgtgtgt gattgcanga catncgaat  gggtacnaga gggcctcagc   360
cgggtctggg tgtncctanc tttggggagg acnncganac agagtggagg tgggaattaa   420
atgacaagtc tgcctttcag aactctngtc accctcaaca ctgagttcac ttcaggtttt   480
tgtttcgtct tgtctcgana cagaatctcc ctctgtcncc caggctggag tgcaatggcc   540
ccntctcngc tcactgcanc nccnccctccc acgttcaagc cnttctcccn gcctcaccttt   600 ccctaaatga ctgngactaa cangtncct  ctggccncc  cggccaacc  ttntttttctc  660 ncnccggttt tcaacnnaaa angggnttcc ccccnttttnt nccncccgc ccccnaacc    720 ccgaaccctt gggccatccc cnctgnctca cnctncccaa attnnnnggg aantnncnna   780
ctctaaccca ccccccccc  tcctnttctt ttttccccct ccccnctct  aaaanacncg   840 gtnancttan acccccngga aaaantttca antcntcatc anccnattnt ctcggctngg   900
ccaaacctaa aattacntgg gaggttaaaa nacncccctc cnaacccctc cctnctcncn   960
actnntcccc ccttcactct ggnngngtnn ngggttccac aacccncacn gnagngggaa  1020
acncncncng nggntngggt tccnccccggg ncnctcgtcc cccncccac  canccccgcn  1080 aattcttcgc actctctcna cnccccggcn cnngtcttct cncgctcntc cccngggnn   1140 aaaaacccgc ggtnctcccc cccctncccn ntnntggnat actctccagg gntcgcctct  1200 ncccctctccc ncnacttcct anccccanca n                                 1231
```

```
<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 6
tggtggctgt ggact                                                    15

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 7
gatgaggatg tgggtctt                                                 18

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 8
ggtggctgtg gactcccca                                                19

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 9
gactgtgcga ggagagcc                                                 18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 10
aggtgaacga cctgcgcg                                                 18

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 11
ctttgcccag aacgcctg                                                 18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Primer
```

-continued

```
<400> SEQUENCE: 12
actcgcgagg cgacttct                                                  18

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 13
ttgcgggaga ggttgtag                                                  18

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 14
ggtttaatcg cgggtctt                                                  18

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 15
cgatcttgta gcccagct                                                  18

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 16
cgaccactca cccattca                                                  18

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 17
tgcaatcaca cacagaga                                                  18
```